United States Patent [19]

Eriks et al.

[11] Patent Number: 5,190,589
[45] Date of Patent: Mar. 2, 1993

[54] COMPOUNDS AND PROCESS PREPARING A SUBSTITUTED OR AN UNSUBSTITUTED 4(5)-(ω-AMINOALKYL)IMIDAZOLE

[75] Inventors: John C. Eriks, Driehuis; Henderikus van der Goot, Hoofddorp; Hendrik Timmerman, Voorschoten; Jan G. Koper, Weesp, all of Netherlands

[73] Assignee: Cedona Pharmaceuticals B.V., Haarlem, Netherlands

[21] Appl. No.: 573,015

[22] PCT Filed: Apr. 5, 1989

[86] PCT No.: PCT/NL89/00019
§ 371 Date: Dec. 3, 1990
§ 102(e) Date: Dec. 3, 1990

[87] PCT Pub. No.: WO89/10360
PCT Pub. Date: Nov. 2, 1989

[30] Foreign Application Priority Data

Apr. 18, 1988 [NL] Netherlands ............... 88 00998

[51] Int. Cl.$^5$ ............... C07D 233/64; C07D 405/10
[52] U.S. Cl. ............... 548/311.7; 548/335.5
[58] Field of Search ............ 548/343, 336, 342; 514/397, 400

[56] References Cited

U.S. PATENT DOCUMENTS 4,119,781 10/1978 Lewis et al. ............... 548/342

OTHER PUBLICATIONS

Durant, et al. *J. Med. Chem.*, vol. 19, No. 7, pp. 923–928 (1976).

Gaudry et al., *Tetrahedron*, vol. 26, No. 23, pp. 5611–5615 (1970).

Elz, et al., *Z.Naturforsch.*, 42b, 238–242 (1987).

*Primary Examiner*—Patricia L. Morris
*Assistant Examiner*—Lenore Miltenberger
*Attorney, Agent, or Firm*—Burgess, Ryan & Wayne

[57] ABSTRACT

A process is provided for preparing novel substituted or unsubstituted 4(5)-ω-aminoalkyl)imidazoles of the formula

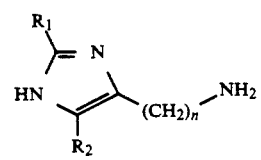

wherein n is 1 to 6, $R_1$ is hydrogen or a linear, branched or cyclic, saturated or unsaturated alkyl group having 1-6 C-atoms or a phenyl ring being unsubstituted, or mono- or di-substituted with groups such as lower alkyl, halogen, alkoxy, methylenedioxy or a combination thereof, and $R_2$ is hydrogen or methyl. The process comprises brominating an ω-phthalimidoalkan-2-one with bromine in anhydrous methanol to a 1- or 3-bromo-ω-phthalimido-alkan-2-one, subjecting said derivative to ring closure with an amidine in N.N-dimethylformamide with potassium carbonate under mild conditions followed by hydrolytic separation of the phthalic residue. Pharmaceutical compounds, compositions and a method of treatment are also provided.

2 Claims, No Drawings

COMPOUNDS AND PROCESS PREPARING A SUBSTITUTED OR AN UNSUBSTITUTED 4(5)-(ω-AMINOALKYL)IMIDAZOLE

BACKGROUND OF THE INVENTION

1. Field of the Invention

The invention relates to a process for preparing a substituted or an unsubstituted 4(5)-(ω-aminoalkyl)imidazole, by brominating an ω-phthalimidoalkan-2-one to a 1- or 3-bromo-ω-phthalimido-alkan-2-one, subjecting said derivative to ring closure with an amidine, followed by hydrolytic separation of the phthalic residue.

2. Description of the Related Art

Such a process is already known from S. Elz and W. Schunack, Z.Naturforsch., 42b, 238–242 (1987).

Histamine $H_2$-receptor agonists, like Impromidine(1) described in Proc. VIIIth Internat. Symp. Med. Chem., Uppsala, pp. 202–203 (1985), editors R. Dahlblom and J. L. G. Nilson, SK&E 91486 (2) described by M. E. Parsons et al., Agents and Actions. 5, 464 (1975) and N-(ω-substituted alkyl)-N'-{(imidazole-4-yl)-alkyl)} guanidines, described in Dutch patent application 86 01585 and indicated therein with formula 1, all contain under physiological conditions a protonated "substituted" N-{ω-(imidazole-4-yl)alkyl}guanidine fragment which is essential for the biological activity of this type of compounds.

For the preparation of these and other $H_1$ and $H_2$-receptor active compounds the 4(5)-(2-aminoethyl)imidazole or histamine (3) and 4(5-(3-aminopropyl)imidazole(4), in general the substituted 4(5)-(ω-aminoalkyl)imidazoles (5) are of crucial importance as starting materials for the preparation of the above mentioned $H_1$ and $H_2$-receptor active compounds, so that in the field of pharmaceutical industry they are highly interested in the preparation of this kind of compounds, in view of pharmaceutical composition for the treatment of heart failures and allergic conditions.

Tedious syntheses of 4(5)-(3-aminopropyl)imidazole (4) starting form one of the two difficult obtainable compounds 4(5)-(2-bromoethyl)imidazolium bromide and 4(5)-(2-chloroethyl)imidazolium chloride as described by W. Bloemhoff, and K. E. T. Kerling, Rec. Trav. Chim., 89, 1181–1184 (1970), followed by chain extension with sodium cyanide or potassium cyanide and by reduction of the obtained nitrile with hydrogen and Raney Nickel catalyst as described in German Offenlegungsschrift 2 053 175, results in almost unacceptable low overall yields of the desired 4(5)-(3-aminopropyl)imidazole (4).

In the process described by S. Elz and W. Schunack Z. Naturforsch., 42b, 238–242 (1987) in the preamble, the bromination of 5-phthalimidopentane-2-one to 1-bromo-5-phthalimidopentane-2-one (6) is carried out in a b-butanol/methanol mixture with an equivalent bromo/dioxane complex which results in a yield of only 22%. The following ring closure in liquid $NH_3$ under elevated pressure, followed by isolation of the desired imidazole via the dipicrate is impracticable in large scale syntheses.

Preparation of the corresponding halogen compounds from the corresponding diazoketones as described by J. Michalsky, J. Borkovec and J. Hadacek, Chem. Listy Vedu Prum. 49, 1979 (1955), cf. Chem. Abstr. 50, 5681d (1956) does not lend itself for large scale syntheses, and the bromination as described by E. W. Garbisch Jr., J. Org. Chem. 30, 2109 (1965) for the 3-phthalimidopropan-2-one, according to M. Gall and B. V. Kamdar, J. Org. Chem. 46, 1575–1585 (1981) does not lend itself for scale enlargement.

Alternatively the ring closure of a 1-bromo-ω-phthalimidoalkan-2-one with an amidine as mentioned for the preparation of 2-methylhistamine under the reaction conditions reported by Durant et al., J. Med. Chem., 19(7), 923–928 (1976) is not very advantageous due to low yields obtained in this procedure.

SUMMARY OF THE INVENTION

It was now found that with the process as described in the preamble a much higher yield can be reached than disclosed in the state of the art, when certain reaction conditions are taken into account towards bromination and the ring closure. In this process the bromination proceeds with great selectively, which enhances the yield highly, in addition the process is suitable for large scale application. The process is practical for a large number of compounds, among which histamine and its analogues, some of which even being novel.

The invention has the characterizing features that in a process as described in the preamble a substituted or unsubstituted 4(5)-(ω-aminoalkyl)imidazole of the formula 5 is prepared, wherein n is 1 to 6, $R_1$ is hydrogen or a linear, branched or cyclic, saturated or unsaturated alkyl group having 1-6 C-atoms or a phenyl ring being unsubstituted, mono- or di substituted with groups such as lower alkyl, nitro and/or amino, if any halogen, alkoxy, methylenedioxy or a combination thereof, and $R_2$ is hydrogen or methyl and the bromination with bromine is carried out in anhydrous methanol and the ring closure is carried in N.N-dimethylformamide with potassium carbonate under mild conditions.

The invention also relates to a pharmaceutical composition that contains a compound obtained according to the just described process. The invention also relates to the use of said compound or pharmaceutical composition as obtained by the earlier mentioned method for the treatment of heart and vasculer diseases or allergic affections.

DESCRIPTION OF THE PREFERRED EMBODIMENTS

The present synthesis proceeds according to the annexed reaction scheme.

As starting materials in the above mentioned reaction scheme ω-phthalimido-2-alkanones (7) are used which can be prepared according to known literature methods.

The bromination of these ketones is performed according to the method for the selective bromination of 2-alkanones as mentioned by M. Gaudry and A. Marquet, Tetrahedron, 26, 5611–5615 (1970) which method gives significantly higher yields of the desired primary bromo compounds (10) in comparison with the method described by S. Elz and W. Schunack, Z.Natur.-forsch.42b, 238–242 (1987).

Depending on the nature of the starting materials the intermediate bromo dimethyl acetals (8) and (9) are isolated and purified before hydrolysis or the total reaction mixture is hydrolysed and the bromo ketones (10) and (11) are separated by fractional crystallization.

Although the secondary bromo ketones (11) are produced with low yields, they have been isolated from the reaction mixture to serve as starting material for the ring closure to 4-(ω-phthalimidoalkyl)-5-methylimidazoles (13) and alternatively they can be obtained in much higher yields by bromination in solvents like acetic acid.

The ring closure of the bromo ketones (10) and (11) together with lower alkane amidines or substituted benzamidines leading to the formation of 4(5)-(ω-phthalimidoalkyl)imidazoles (12) and corresponding methyl derivatives (13) is performed in N.N-dimethylformamide with potassium carbonate as proton acceptor under mild conditions.

Hydrolysis of the compounds (12) and (13) with diluted hydrochloric acid as described in U.S. Pat. No. 3,736,331, or hydrazinolysis with hydrazine hydrate as described by M. Gall and B. V. Kamdar, J. Org. Chem. 46, 1575–1585 (1981) provides 4(5)-(ω)-aminoalkyl) imidazoles (5).

The invention is illustrated by the following examples.

All chemicals and solvents are commercially available unless otherwise stated.

Melting points were determined with a Mettler FP 52 melting point apparatus.

$^1$H-NMR-spectra were measured with a Bruker WH-90 spectrophotometer and chemical shifts δ (in ppm) are given relative to tetramethylsilane.

Mass spectra are recorded on a Varian Mat CH$_5$ spectrometer.

EXAMPLE I a. 4-Phthalimidobutan-2-one (7a)

The 4-phthalimidobutan-2-one is prepared according to a modified procedure as mentioned by H. Irai et al., Kogyo Kagaku Zasshi., 62, 82–85 (1959); cf. Chem. Abstr., 58, 5659b (1963).

To a well stirred suspension of 147 g (1 mole) of phthalimide and 70 g (1 mole) of methyl vinyl ketone in 1000 ml ethyl acetate is added under nitrogen a freshly prepared solution of 2.7 g (0.05 mole) of sodium methoxide in 250 ml anhydrous methanol.

After stirring for two hours at room temperature the mixture is heated until reflux temperature and refluxed until an almost clear solution is obtained and refluxing is continued for an additional two hours.

The solution is allowed to cool down and concentrated in vacuum and the residue is recrystallized from hot 96% ethanol.

Yield 90%.

Melting point 108.5°–110.0° C. (Lit: H. Irai et al., 111°–113° C.).

$^1$H-NMR (CDCl$_3$): 2.22 ppm., singlet, 3H; 2.96 ppm., triplet (J=7 Hz), 2H; 3.96 ppm., triplet (J=7 Hz), 2H; 7.62–7.96 ppm., multiplet, 4H.

b. 1-Bromo-4-phthalimidobutan-2-one (10a)

To a suspension of 130 g (0.6 mole) of 4-phthalimido butan-2-one (7a) in 1000 ml of absolute methanol is added 96 g (0.6 mole) of bromine and the reaction mixture is stirred for 24 hours at room temperature.

The precipitate, N-(4-bromo-3.3-dimethoxybutyl) phthalimide (8a) is filtered off, suspended in methanol and 30 ml of 10N sulfuric acid is added, after which the reaction mixture is heated until a clear solution is obtained.

After cooling down the precipitate is collected and recrystallized from hot methanol.

Yield 60%.

Melting point: 120°–122° C. (lit: R. G. Jones et al., J. Am. Chem. Soc., 72, 4526–4529 (1950), 119°–120° C.).

$^1$H-NMR (CDCl$_3$): 3.13 ppm., triplet, 2H (J=7.2 Hz); 3.92 ppm., singlet, 2H; 4.04 ppm., triplet (J=7.2 Hz), 2H; 7.60–7.96 ppm., multiplet, 4H.

c. 4(5)-(2-phthalimidoethyl)imidazole (12a)

A mixture of 29.6 g (0.1 mole) of 1-bromo-4-phthalimido-butan-2-one (10a), 10.4 g (0.1 mole) formamidine acetate, 27.6 g (0.2 mole) of carefully ground anhydrous potassium carbonate and 150 ml of anhydrous N.N-dimethylformamide is slowly heated in a shaking autoclave for about 24 hours to 80° C.

After cooling down the solid inorganic materials are filtered off and the filtrate is concentrated in vacuum. To the residue 50 ml of xylene is added and again concentrated in vacuum to remove traces of N.N-dimethylformamide, after which the residue is taken up in 200 ml of ethyl acetate and extracted three times with 50 ml of demineralized water.

The organic layer is dried on anhydrous sodium sulfate, filtered and concentrated in vacuum.

The residue is taken up in acetone and a saturated solution of oxalic acid in acetone is added until no more precipitation occurs.

The precipitate is filtered off, washed with three portions of warm acetone and dried in vacuum.

Yield 60%.

Melting point: the oxalate decomposes on heating.

$^1$H-NMR$^{*1}$ (CDCl$_3$/d$_6$-DMSO): 2.91 ppm., triplet (J=7.2 Hz), 2H; 3.96 ppm., triplet (J=7.2 Hz), 2H+; 6.84 ppm., singlet, 1H; 7.63 ppm., singlet, 1H; 7.74 ppm., broad singlet, 4H; 8.12 ppm., broad singlet, 1H. *$^1$free base d. 4(5)-(2-Aminoethyl)imidazoledihydrochloride (histaminedihydrochloride) (5a)

The 4(5)-(2-aminoethyl)imidazole dihydrochloride is prepared by hydrolysis of 4(5)-(2-phthalimidoethyl-)imidazole (12a) according to U.S. Pat. No. 3,736,331.

A solution of 16.55 g (0.05 mole) of 4(5)-(2-phthalimidoethyl)imidazole (12a) oxalate is dissolved in 200 ml of distilled water and brought to pH=12 with a diluted sodium hydroxide solution. The base is extracted with ethyl acetate, and the organic layer is dried on anhydrous sodium sulfate, filtered and concentrated in vacuum.

The residue is hydrolyzed by refluxing with 5N hydrochloric acid and after cooling down the volume is reduced in vacuum, the phthalic acid is filtered off and the filtrate is concentrated to dryness, after which the residue is recrystallized from hot ethanol.

Yield 85%.

Melting point 249°–252° C.

$^1$H-NMR (D$_2$O): 3.38–3.80 ppm., multiplet, 4H; 7.72 ppm., doublet (J=0.6 Hz), 1H; 8.98 ppm., doublet (J=1 Hz), 1H.

EXAMPLE II a. 5-Phthalimido pentan-2-one (7b)

5-Phthalimidopentan-2-one is prepared according to a modified procedure as mentioned by M. Sletzinger et al., Chem., & Ind. (London), 1957, 1215.

A mixture of 294 g (2 moles) of phthalimide, 241 g (2 moles) of 5-chloropentan-2-one and 198 g (2 moles) of carefully ground anhydrous potassium carbonate in 1000 ml of anhydrous N.N-dimethylformamide was heated while stirring for a period of 12 hours at 110° C.

After cooling down the inorganic solids were filtered off and the filtrate was concentrated in vacuum.

The residue was dissolved in 500 ml ethyl acetate and after standing overnight at 0° C. the unreacted phthalimide was filtered off, the filtrate was concentrated in vacuum and the residue was recrystallize from hot methanol.

Yield 53%.

Melting point: 72°–74° C. (Lit: M. Sletzinger et al., 75°–77° C.; S. Elz and W. Schunack, Z.Natur.Forsch., 42b, 238–242 (1987), 71°–72° C).

$^1$H-NMR (CDCl$_3$): 1.89–2.12 ppm., multiplet, 2H; 2.15 ppm., singlet, 3H; 2.51 ppm., triplet (J=7.2 Hz), 2H; 3.72 ppm., triplet (J=6.6 Hz), 2H; 7.67–7.92 ppm., multiplet, 4H.

b. 1-Bromo-5-phthalimidopentan-2-one (10b)

To a solution of 231 g (1 mole) of 5-phthalimidopentan-2-one (7b) in 1350 ml of anhydrous methanol was added at 0° C. in one portion 160 g (1mole) of bromine.

While stirring, the mixture was allowed to warm up to ambient temperature and stirring was continued for an additional 24 hours.

To the clear solution 200 ml of 10N sulfuric acid was added and the reaction mixture was left overnight.

The precipitate was collected, suspended in 500 ml of methanol and refluxed for 15 minutes and the crystalline material was filtered off while hot, washed with two portions of 100 ml of hot methanol and dried in vacuum.

Yield 52%.

Melting point: 131°–133.4° C. (Lit: S. Elz and W. Schunack, Z.Natur.forsch. 42b, 238–242 (1987), 122°–125° C., J. Michalksky et al., Chem.Listy, 49, 1379–1384 (1955), cf. Chem.Abstr. 50, 5681 d (1956), 139° C.

$^1$H-NMR (CDCl$_3$): 1.82–2.24 ppm., multiplet, 2H; 2.74 ppm.., triplet (J=7.2 Hz), 2H; 3.74 ppm., triplet (J=7.2 Hz), 2H; 3.94 ppm., singlet, 2H; 7.64–7.88 ppm., multiplet, 4H.

c. 4(5)-(3-Phthalimidopropyl)imidazole (12b)

A mixture of 114.0 g (0.37 mole) of 1-bromo-5-phthalimidopentan-2-one (10b), 38.3 g (0.37 mole) of formamidine acetate, 101.5 g (0.74 mole) of carefully ground anhydrous potassium carbonate and 500 ml of anhydrous N.N-dimethylformamide is slowly heated in a shaking autoclave for 24 hours at 80° C. After cooling down the solid inorganic materials are filtered off and the filtrate is concentrated in vacuum. To the residue 200 ml of xylene is added and it is again concentrated in vacuum to remove traces of N.N-dimethylformamide, after which the residue is taken up in 750 ml of ethyl acetate and is extracted three times with 100 ml of demineralized water.

The organic layer is dried on anhydrous sodium sulfate, filtered and concentrated in vacuum.

The residue is taken up in acetone and a saturated solution of oxalic acid in aceton is added until no more precipitation occurs.

The precipitate is filtered off, washed with warm aceton and dried in vacuum.

Yield 55%.

Melting point: the oxalate decomposes on heating.

$^1$H-NMR* (CDCl$_3$): 1.80–2.21 ppm., quintet (J=7.2 Hz), 2H; 2.60 ppm., triplet (J=7.2 Hz), 2H; 3.68 ppm., triplet (J=7.2 Hz), 2H; 6.81 ppm., singlet, 1H; 7.54 ppm., singlet, 1H; 7.54–7.85 ppm., multiplet, 4H. Position of NH-proton strongly depends on concentration.
*free base.

d. 4(5)-(3-Aminopropyl)imidazole dihydrochloride (5b)

4(5)-(3-aminopropyl)imidazole (5b) dihydrochloride is prepared by hydrolysis of 4(5)-(3-phthalimidopropyl)imidazole (12b) according to U.S. Pat. No. 3,736,331.

A solution of 17.25 g (0.05 mole) of 4(5)-(3-phthalimidopropyl)imidazole (12b) oxalate is prepared in 200 ml of distilled water and brought on pH=12 with a diluted sodium hydroxide solution. The base is extracted with ethyl acetate and the organic layer is dried on anhydrous sodium sulfate, filtered and concentrated in vacuum.

The residue is hydrolyzed by refluxing with 5N hydrochloric acid and after cooling down the volume is reduced in vacuum, the phthalic acid is filtered off and the filtrate is concentrated to dryness, after which the residue is recrystallized from ethanol/ether.

Yield 92%.

Melting point: 154°–155° C. (Lit: J. W. Black et al, U.S. Pat. No. 3,736,331, 156°–158° C.).

$^1$H-NMR (d$_6$-DMSO): 1.80–2.13 ppm., multiplet, 2H: 2.80 ppm., broad triplet (J=7.2 Hz), 4H; 2.8H; 7.52 ppm., doublet (J=0.6 Hz), 1H; 8.30 ppm., broad singlet, 2.6H, 9.14 ppm., doublet (J=1Hz), 1H.

EXAMPLE III

3-Bromo-4-phthalimidobutan-2-one (11b)

The filtrate obtained after the removal of N-(4-bromo-3.3-dimethoxybutyl)phthalimide (8a) in example Ib is treated with diluted sulfuric acid and worked up as mentioned for the preparation of 1-bromo-4-phthalimidobutan-2-one (10a) in the same example.

Yield 30%.

Melting point: 104°–105° C.

$^1$H-NMR (CDCl$_3$): 2.46 ppm., singlet, 3H; 4.16–4.28 ppm.,. double doublet, 2H; 4.76–4.92 ppm., broad triplet, 1H; 7.71–7.95 ppm., multiplet, 4H.

EXAMPLE IV a. 3- Bromo-5-phthalimidopentan-2-one (11b)

The mother liquor obtained after the filtration of the 1-bromo-5-phthalimidopentan-2-one (10b) in example IIb was concentrated to approximately half of its original volume and the precipitate was filtered off and recrystallized from hot methanol.

Yield 35%.

Melting point 99.0°–100.7° C.

$^1$H-NMR (CDCl$_3$): 2.22–2.70 ppm., multiplet, 2H; 2.42 ppm., singlet, 3H; 3.80 ppm., triplet (J=6.6 Hz), 2H; 4.34 ppm., triplet (J=7.2 Hz), 1H; 7.66–7.90 ppm., multiplet, 4H.

Mass spectrum M/Z (% rel., fragm.): 267(20) 230(99), 188(47), 174(52) 161(94), 160(100), 148(23), 133(20), 104(43).

M$^+$=M/Z 309.0006 calculated C$_{13}$H$_{12}$BrNO$_3$ 309.0001 b. 4-methyl-5(2-phthalimidoethyl(imidazole

A mixture of 31.0 g (0.1 mole) of 3-bromo-5-phthalimidopentan-2-one (11b), 10.4 g (0.1 mole) of formamidine acetate, 27.6 g (0.2 mole) of carefully ground anhydrous potassium carbonate and 150 ml of anhydrous N.N-dimethylformamide is heated in a shaking autoclave at 80° C. for 24 hours.

After cooling down the solid inorganic materials are filtered off and the filtrate is concentrated in vacuum. To the residue 50 ml of xylene is added and it is again concentrated in vacuum to remove traces of N.N-dimethylformamide, after which the residue is taken up in 200 ml of ethyl acetate and extracted three times with 50 ml of demineralized water.

The organic layer is dried on anhydrous sodium sulfate, filtered and concentrated in vacuum.

The residue is taken up in acetone and the mixture is allowed to crystallize.

The precipitate is filtered off, washed with 3 portions of warm acetone and dried in vacuum.

Yield 70%.

Melting point: 197.0°–198.5° C.

$^1$H-NMR (CDCl$_3$/d$_6$-DMSO): 2.10 ppm., singlet, 3H; 2.90 ppm., triplet (J=7.2 Hz), 2H; 3.90 ppm., triplet (J=7.2 Hz), 2H; 7.40 ppm, singlet, 1H; 7.43 ppm., singlet, 0.7H; 7.64–7.85 ppm., multiplet, 4H. Mass spectrum M/Z (% rel., fragm.): 255(37), 230(5), 174(52), 160(33), 108(100), 95(92).

M$^+$=M/Z 255.1021 calculated C$_{14}$H$_{13}$N$_3$O$_2$ 255.1008.

c. 4-(2-Aminoethyl)-5-methylimidazole dihydrochloride (5c)

4-(2-Aminoethyl)-5-methylimidazole dihydrochloride is prepared by hydrolysis of 4-methyl-5(2-phthalimidoethyl) imidazole (13a) according to U.S. Pat. No. 3,736,331.

A solution of 15.3 g (0.06 mole) 4-(2-phthalimidoethyl)-5-methylimidazole (13a) in 150 ml 5N hydrochloric acid is heated under reflux for 5 hours and after cooling down the volume is reduced in vacuum, the phthalic acid is filtered off and the filtrate is concentrated to dryness, after which the residue is recrystalized from ethanol/ether.

Yield 86%. Melting point: hydrochloride decomposes on heating.

$^1$H-NMR (D$_2$O/DMSO): 2.15 ppm., singlet, 3H; 3.25–3.70 ppm., broad singlet, 4H; 7.40 ppm., singlet, 1H.

EXAMPLE V a. 2.5-dimethyl 4-(2-phthalimidoethyl) imidazole (13b)

A mixture of 31.0 g (0.1 mole) of 3-bromo-5-phthalimidopentan-2-one (11b), 11.8 g (0.1 mole) of acetamidine acetate, 27.6 g (0.2 mole) of carefully ground anhydrous potassium carbonate and 150 ml of anhydrous N.N-dimethylformamide is heated in a shaking autoclave at 80° C. for 24 hours.

After cooling down the solid organic materials are filtered off and the filtrate is concentrated in vacuum. To the residue 50 ml of xylene is added and it is again concentrated in vacuum to remove traces of N.N-dimethylformamide, after which the residue is taken up in 200 ml of ethyl acetate and extracted three times with 50 ml of demineralized water.

The organic layer is dried on anhydrous sodium sulfate, filtered and concentrated in vacuum.

The residue is taken up in acetone and a saturated solution of oxalic acid in acetone is added until no more precipitation occurs.

The precipitate is filtered off, washed with three portions of warm acetone and dried in vacuum.

Yield 40%.

Melting point: the oxalate decomposes on heating.

$^1$H-NMR* (CDCl$_3$/d$_6$-DMSO): 2.10 ppm., singlet, 3H; 2.25 ppm., singlet, 3H; 2.90 ppm., triplet (J=7.2 Hz), 2H; 3.90 ppm., triplet (J=7.2 Hz), 2H; 7.43 ppm., singlet, 0.7H; 7.64–7.85 ppm., multiplet, 4H.
*free base b. 4-(2-Aminoethyl(-2,5-dimethylimidazole dihydrochloride (5d).

4-(2-Aminoethyl)-5-methylimidazole dihydrochloride (5d) is prepared by hydrolysis of 2.5-dimethyl 4-(2-phthalimid ethyl)-imidazole (13b) according to U.S. Pat. No. 3,736,331.

A solution of 9.4 g (0.035 mole) 2.5-dimethyl 4(2-phthalimidoethyl)-imidazole (13b) oxalate in 200 ml distilled water is brought on pH=12 with diluted sodium hydroxide solution. The base is extracted with ethyl acetate and the organic layer is dried on anhydrous sodium sulfate, filtered and concentrated in vacuum.

The residue is hydrolyzed by refluxing with 5N hydrochloric acid and after cooling down the volume is reduced in vacuum, the phtalic acid is filtered off and the filtrate is concentrated to dryness, after which the residue is recrystallized from ethanol/ether.

Yield 91%.

Melting point: the hydrochloride decomposes on heating. $^1$H-NMR (D$_2$O/DMSO):2.10 ppm., singlet, 3H; 2.38 ppm, singlet, 3H; 3.23–3.65 ppm., broad singlet, 4H.

EXAMPLE VI a. 2-Phenyl-4(5)-(2-phthalimidoethyl)imidazolehydrochloride (13c)

A mixture of 12.0 g (0.1 mole) benzamidine, 29.6 g (0.1) mole 1-bromo-4-phthalimidobutan-2-one (10a), 27.6 g (0.2 mole) of carefully ground anhydrous potassium carbonate and 125 ml of anhydrous N.N-dimethylformamide is heated under stirring at 35° C. for 24 hours, after which it is subsequently heated at 50° C. for 2 hours.

After cooling down the reaction mixture is concentrated in vacuum, after which to the residue demineralized water is added. Subsequently it is extracted 3 times with 50 ml ethyl acetate, the combined organic phases are collected, dried on anhydrous sodium sulfate, filtered and concentrated in vacuum.

To the residue a circa 3%-hydrochloric acid-solution is added and under stirring carefully heated to 40° C. After cooling down the precipitate is filtered off and dried in vacuum, after which it is crystallized from methanol.

Yield 40%.

Melting point: 222.0°–225.0° C. (dec.) $^1$H-NMR (d$_6$-DMSO): 3.23 ppm., triplet (J=7.5 hz), 2H, 4.13 ppm., triplet (J=7.5 Hz), 2H; 7.60–7.87 ppm., multiplet, 4H; 8.00 ppm., singlet, 4H; 8.20–8.40 ppm., multiplet, 2H; 15.17 ppm., broad singlet, 1.4H.

b. 4(5)-(2-aminoethyl)2-phenyl-imidazole-dihydro chloride (5e)

A solution of 12.4 g (0.035 mole) 2-phenyl-4(5)-(2-phthalimidoethyl)imidoethyl)imidazole hydrochloride (13c) and 8.8 g (0.175 mole) hydrazine hydrate in 150 ml absolute ethanol is heated under reflux for 5 hours.

After cooling down and after standing overnight the crystalline material is filtered off, after which the filtrate is concentrated in vacuum.

The residue was taken up in 50 ml of absolute ethanol and by means of a concentrated hydrochloric acid solution acidified to acid reaction, after which the precipitate is filtered off.

Subsequently the precipitate is recrystallized from ethanol/water.

Yield 85%.

Melting point: 268.9°–271.0° C. (dec.)

$^1$H-NMR (d$_6$-DMSO): 3.00–3.50 ppm., multiplet, 4H; 7.50–7.75 ppm., multiplet, 4H; 8.00–8.55 ppm., multiplet, 5H; 15.16 ppm., broad singlet, 2H.

EXAMPLE VII a.
2-(4-chlorophenyl)-4(5)-(2-phthalimidoethyl)-imidazole hydrochloride (13d)

A mixture of 15.4 g (0.1 mole) of 4-chlorobenzamidine, 29.6 g (0.1 mole) of 1-bromo-4-phthalimidobutan-2-one (10a), 27.6 g (0.2 mole) of carefully grounded anhydrous potassium carbonate and 125 ml anhydrous N.N-dimethyl formamide is heated while stirring at 35° C. for 24 hours, after which heating at 50° is continued for 2 hours.

After cooling down the reaction mixture is concentrated in vacuum, after which demineralized water is added to the residue.

Subsequently there is extracted three times with 50 ml of ethyl acetate, the combined organic phases are collected, dried on anhydrous sodium sulfate, filtered and concentrated in vacuum.

To the residue a circa 3%-hydrochloric acid-solution is added and while stirring carefully heated to 40° C.

After cooling down the precipitate is filtered off and dried in vacuum, after which it is crystallized from an ethanol/ether mixture.

Yield 54%.

Melting point: 250° C. (dec.)

$^1$H-NMR (D$_6$-DMSO): 3.15 ppm., triplet (J=7.5 Hz), 2H; 4.00 ppm., triplet (J=7.5 Hz), 2H; 7.70–8.20 ppm., multiplet, 9H; 14.50 ppm., broad singlet, 2H.

b. 4(5)-(2-Aminoethyl)-2-(4-chlorophenyl)imidazole dihydrochloride (5f)

A solution of 19.4 g (0.050 mole) of 2-(4-chlorophenyl)-4(5)-(2-phthalimidoethyl)imidazole hydrochloride (13d) and 12.5 g (0.0250 mole) of hydrazine hydrate in 150 ml of absolute ethanol is heated under reflux for 5 hours.

After cooling down and after standing overnight the crystalline material is filtered off, after which the filtrate is concentrated in vacuum.

The residue is subsequently taken up in 50 ml of absolute ethanol and by means of concentrated hydrochloric acid solution acidified to acid reaction, after which the precipitate is filtered off.

Thereafter recrystallization takes place from an ethanol/water mixture.

Yield 92%

Melting point: 191.3°–195.6° C. (dec.)

$^1$H-NMR (d$_6$-DMSO): 2.90–3.60 ppm., multiplet, 4H; 7.50 ppm., singlet, 1H; 7.80 ppm., doublet (J=9.0 Hz), 2H; 7.90–8.20 ppm., broad multiplet, 5H; 15.10 ppm., broad singlet, 2H.

EXAMPLE VIII a.
2-(4-methoxyphenyl)4(5)-(2-phthalimidoethyl)imidazole hydrochloride (13e)

A mixture of 15.0 g (0.1 mole) of 4-methoxybenzamidine, 29.6 g (0.1 mole) of 1-bromo-4-phthalimidobutan-2-one (10a), 27.6 g, (0.2 mole) of carefully ground anhydrous potassium carbonate and 125 ml of anhydrous N.N-dimethyl formamide is heated while stirring at 35° C. for 24 hours, after which the heating is continued at 50° C. for 2 hours.

After cooling down the reaction mixture is concentrated in vacuum, after which to the residue demineralized water is added.

There is extracted three times with 50 ml ethyl acetate, the combined organic phases are collected, dried on anhydrous sodium sulfate, filtered and concentrated in vacuum. To the residue a circa 3%-hydrochloric acid solution is added and carefully heated while stirring to 40° C. After cooling down the precipitate is filtered off and dried in vacuum, after which it is crystallized from an ethanol/ether mixture.

Yield 50%

Melting point: 191.3°–195.6° C. (dec.) $^1$H-NMR (d$_6$-DMSO): 2.90–3.60 ppm., multiplet, 4H; 7.50 ppm., singlet, 1H; 7.80 ppm., doublet (J=9.0 Hz), 2H; 7.90–8.20 ppm., broad multiplet, 5H; 15.10 ppm., broad singlet, 2H.

EXAMPLE VIII

4(5)-2-Aminoethyl)-2-(4-methoxyphenyl)imidazole dihydrochloride (5 g)

A solution of 17.3 g (0.0045 mole) of 4(5)-2-(4-methoxyphenyl)-(2-phthalimidoethyl)imidazole hydrochloride (13e) and 11.3 g (0.225 mole) of hydrazine hydrate in 150 ml of absolute ethanol is heated under reflux for 5 hours.

After cooling down and after standing overnight the crystalline material is filtered off, after which the filtrate is concentrated in vacuum.

The residue is taken up in 50 ml of absolute ethanol and acidified by means of a concentrated hydrochloric acid solution to acid reaction, after which the precipitate is filtered off. Thereafter there is crystallized from an ethanol/water mixture.

Yield 80%.

Melting point: 219.0°–221.5° C. $^1$H-NMR (d$_6$-DMSO): 3.06–3.57 ppm., broad triplet, 4H; 4.00 ppm., singlet, 3H; 7.32 ppm., doublet (J=9.0 Hz) 2H; 7.67 ppm., singlet, 1H; 8.19–8.63 ppm., broad singlet, 3H; 8.35 ppm., doublet (J=9.0 Hz), 2 H; 15.06 ppm., broad doublet, 2H.

EXAMPLE IX a.
2-(3.4-methylene-dioxyphenyl)4(5)-(2-phthalimidoethyl)-imidazole hydrochloride (13f)

A mixture of 16.4 g (0.1 mole) of 3.4-methylenedioxybenzamidine, 29.6 g (0.1 mole) of 1-bromo-4-phthalimidobutan-2-one (10a), 27.6 g (0.2 mole) of carefully grounded anhydrous potassium carbonate and 125 ml of anhydrous: N.N-dimethyl formamide is heated while stirring at 35° C. for 24 hours, after which the heating is continued at 50° C. for 2 hours.

After cooling down the reaction mixture is concentrated in vacuum, after which to the residue demineralized water is added. The residue is extracted three times with 50 ml of ethyl acetate, the combined organic phases are collected, dried on anhydrous sodium sulfate, filtered and concentrated in vacuum.

To the residue a circa 3%-hydrochloric acid solution is added, while stirring it is carefully heated to 40° C.

After cooling down the precipitate is filtered off and dried in vacuum, after which it is crystallized from an ethanol/ether mixture.

Yield 55%.

Melting point 241.8°–245.9° C. (dec.). $^1$H-NMR (d$_6$-DMSO): 3.12 ppm., triplet (J=7.5 Hz), 2H; 4.05 ppm., triplet (J=7.5 Hz), 2H; 6.27 ppm., singlet, 2H; 7.28 ppm., double (J=9.0 Hz), 1H; 7.60 ppm., singlet, 1H; 7.66 ppm., multiplet, 3H; 7.93 ppm., singlet, 4H; 14.85 ppm., broad singlet, 2H.

b.
4(5)-(2-Aminoethyl)-2-(3.4-methylenedioxyphenyl)imidazole dihydrochloride (5h)

A solution of 19.9 g (0.050 mole) or 2-(3.4-methylene dioxyphenyl)4(5)-(2-phthalimidoethyl)imidazole hydrochloride (13f) and 12.5 g (0.025 mole) of hydrazinehydrate in 150 ml of absolute ethanol is heated under reflux for 5 hours.

After cooling down and after standing overnight the crystalline material is filtered off, after which the filtrate is concentrated in vacuum.

The residue is taken up in 50 ml of absolute ethanol and acidified with the aid of a concentrated hydrochloric acid solution to acid reaction, after which the precipitate is filtered off.

Then the residue is recrystallized from an ethanol/water mixture.

Yield 90%

Melting point: 250.0°–255.0° C. (dec.) $^1$H-NMR (d$_6$-DMSO): 2.86–3.60 ppm., multiplet 4H; 6.16 ppm., singlet, 2H; 7.16 ppm., doublet (J=9.0 Hz), 1H; 7.50 ppm., singlet, 1H; 7.88 ppm., doublet (J=9.0 Hz), 1H; 8.00 ppm., singlet, 1H; 8.40 ppm., broad singlet, 3H; 15.27 ppm., broad singlet, 1H.

EXAMPLE X a. 2-(3,4-dimethoxy-phenyl)imidazole 4(5)-(2-phthalimidoethyl) hydrochloride (13 g)

A mixture of 18.0 g (0.1 mole) of 3.4-dimethoxybenzamidine, 29.6 g (0.1 mole) of 1-bromo-4-phthalimidobutan-2-one (10a), 27.6 g (0.2 mole) of carefully ground anhydrous carbonate and 125 ml of of anhydrous N.N-dimethylformamide is heated while stirring at 35° C. for 24 hours, after which the heating is continued at 50° C. for 2 hours.

After cooling down the reaction mixture is concentrated in vacuum, after which to the residue demineralized water is added.

The residue is extracted three times with 50 ml ethyl acetate. The combined organic phases are collected, dried on anhydrous sodium sulfate, filtered and concentrated in vacuum.

To the residue a circa 3%-hydrochloric acid solution is added and carefully heated while stirring to 40° C.

After cooling down the precipitate is filtered off and dried in vacuum, after which it is crystallized from an ethanol/ether mixture.

Yield 52%

Melting point: 208.5°–211.9° C. (dec.) $^1$H-NMR (d$_6$-DMSO): 3.14 ppm., triplet (J=7.5 Hz), 2H; 3.50–4.40 ppm., broad multiplet, 8H; 7.20–8.20 ppm., multiplet, 7H; 15.00 ppm., broad singlet, 2H.

b.
4(5)-2-Aminoethyl)-2-(3.4-dimethoxyphenyl-imidazole dihydrochloride (5i)

A solution of 20.7 g (0.050 mole) 2-(3.4-dimethoxyphenyl)4(5)-(2-phthalimidoethyl imidazole hydrochloride (13 g) and 12.5 g (0.025 mole) hydrazine hydrate in 150 ml of absolute ethanol is heated under reflux for 5 hours.

After cooling down and after standing overnight the crystalline material is filtered off, after which the filtrate is concentrated in vacuum.

The residue is taken up in 50 ml of absolute ethanol and with a concentrated hydrochloric acid solution acidified t acid reaction, after which the precipitate is filtered off.

Then the residue is recrystallized from an ethanol/water mixture.

Yield 85%.

Melting point: 254.8°–265.8° C. )dec.) $^1$H-NMR (d$_6$-DMSO): 2.90–3.51 ppm., broad triplet, 4H; 3.88 ppm., singlet, 3H; 3.92 ppm., singlet, 3H; 7.20 ppm., doublet (J=9.0 Hz, 1H; 7.53 ppm., singlet, 1H; 7.87 ppm., doublet (J=9.0 Hz), 1H; 8.05 ppm., singlet, 1H; 8.25 ppm., broad singlet, 3H; 15.00 ppm., broad doublet, 2H.

EXAMPLE XI a.
2-(4-methylphenyl)-4(5)-2(phthalimidoethyl)imidazole hydrochloride (13h).

A mixture of 13.4 g (0.1 mole) 4-methyl benzamidine, 29.6 g (0.1 mole) 1-bromo-4-phthalimido-butan-2-one (10a), 27.6 g (0.2 mole) of carefully ground anhydrous potassium carbonate and 125 ml of anhydrous N.N-dimethylformamide is heated while stirring at 35° C. for 24 hours, after which the heating is continued at 50° C. for 2 hours.

After cooling down the reaction mixture is concentrated in vacuum, after which demineralized water is added to the residue.

The residue is three times extracted with 50 ml ethyl acetate, the combined organic phases are collected, dried on anhydrous sodium sulfate, filtered and concentrated in vacuum.

To the residue a circa 3%-hydrochloric acid solution is added and carefully heated under stirring to 40° C.

After cooling down the precipitate is filtered off and dried in vacuum, after which it is crystallized from an ethanol/ether mixture.

Yield 60%.

Melting point: 238° C. (dec.) $^1$H-NMR (d$_6$-DMSO): 2.40 ppm., singlet, 3H; 3.23 ppm., triplet, (J=7.5 Hz), 2H; 4.15 ppm., triplet (J=7.5 Hz), 2H; 7.49 ppm., doublet (J=9.0 Hz), 2H; 7.71 ppm., doublet (J=9.0 Hz), 2H; 7.80–8.10 ppm., broad singlet, 5H; 15.15 ppm., broad singlet, 2H.

b. 4(5)-2-Aminoethyl)2-(4-methylhenyl)imidazole dihydrochloride (5j)

A solution of 18.4 g (0.050 mole) 2-(4-methylphenyl)4(5)-(2-phthalimidoethyl)imidazole hydrochloride (13h) and 12.5 g (0.25 mole) of hydrazine hydrate in 150 ml of absolute ethanol is heated under reflux for 5 hours.

After cooling down and after standing overnight the crystalline material is filtered off, after which the filtrate is concentrated in vacuum.

The residue is taken up in 50 ml of absolute ethanol and with a concentrated hydrochloric acid solution acidified to acid reaction, after which the precipitate is filtered off.

Then the precipitate is recrystallized from an ethanol/water mixture.

Yield 80%.

Melting point: 232.2°-236.5° C. (dec.) $^1$NMR ($D_2O$): 2.42 ppm., singlet, 3H; 3.04-3.54 ppm., multiplet, 4H; 7.38 ppm., singlet, 1H; 7.47 ppm., doublet (J=9.0 Hz), 2H; 7.76 ppm., doublet (J=9.0 Hz), 2H,

We claim:

1. A process for preparing a substituted or an unsubstituted 4(5)-ω-aminoalkyl)imidazole of the formula:

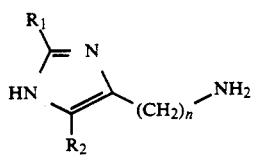

wherein n has a value of from 2 to 6; $R_1$ is hydrogen or a linear, branched or cyclic, saturated or unsaturated non-aromatic hydrocarbon group having 1-6 C-atoms or a substituted or unsubstituted phenyl group wherein any substituents are mono- or di-substituents selected from the group consisting of lower alkyl, halogen, alkoxy and methylenedioxy or a combination thereof, and $R_2$ is hydrogen or methyl;

said process comprising brominating an ω-phthalimidoalkan-2-one to form a 1- or 3-bromo-ω-phthalimido-alkan-2-one derivative, subjecting said derivative to ring closure with an amidine, followed by hydrolytic separation of the phthalic residue, and wherein the bromination is carried out in an anhydrous methanol and the ring closure is carried out in N.N-dimethylformamide with potassium carbonate under mold conditions.

2. A compound of the formula

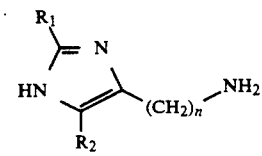

wherein n has a value of from 2 to 6; $R_1$ is a branched or cyclic, saturated non-aromatic hydrocarbon group having 3-6 C-atoms, a linear, branched or cyclic unsaturated non-aromatic hydrocarbon group having 2-6 carbon atoms or a substituted or unsubstituted phenyl group wherein any substituents are mono- or di-substituents selected from the group consisting of lower alkyl, halogen, lower alkoxy and methylenedioxy or a combination thereof, and $R_2$ is hydrogen or methyl.

* * * * *